United States Patent
Feng et al.

(10) Patent No.: US 11,413,192 B2
(45) Date of Patent: *Aug. 16, 2022

(54) HEMOSTATIC PASTE AND METHODS OF MAKING THEREOF

(71) Applicants: Guangzhou Bioseal Biotech Co., Ltd., Guangzhou Science (CN); Johnson & Johnson China Ltd., Shanghai (CN); Ethicon, Inc., Somerville, NJ (US)

(72) Inventors: Dengmin Feng, Guangzhou (CN); Ling Teng, Guangzhou (CN); Yanhui Zhang, Shanghai (CN); Guojun Ni, Hangzhou (CN); Yufu Li, Bridgewater, NJ (US); Xiang Wan, Basking Ridge, NJ (US)

(73) Assignees: Guangzhou Bioseal Co., Ltd., Guangzhou Science (CN); Johnson & Johnson China Ltd., Shanghai (CN); Ethicon Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/912,659

(22) Filed: Jun. 25, 2020

(65) Prior Publication Data
US 2020/0323690 A1  Oct. 15, 2020

Related U.S. Application Data

(62) Division of application No. 16/055,433, filed on Aug. 6, 2018, now Pat. No. 10,736,786.

(30) Foreign Application Priority Data

Jul. 20, 2018  (CN) .......................... 201810851056.6

(51) Int. Cl.
*A61F 13/00* (2006.01)
*A61L 15/28* (2006.01)
(Continued)

(52) U.S. Cl.
CPC ........ *A61F 13/00012* (2013.01); *A61L 15/28* (2013.01); *A61L 15/425* (2013.01);
(Continued)

(58) Field of Classification Search
CPC .... C08L 1/26; C08L 1/286; C08L 1/02; A61L 15/60; A61L 15/425; A61L 15/28;
(Continued)

(56) References Cited

U.S. PATENT DOCUMENTS 2,772,999 A    12/1956  Masci
3,328,259 A     6/1967  Anderson
(Continued)

FOREIGN PATENT DOCUMENTS

CN    1169291 A    1/1998
CN  101001649 A    7/2007
(Continued)

OTHER PUBLICATIONS

PE2E Translated CN 104349797 A (Year: 2015).*
(Continued)

*Primary Examiner* — Blessing M Fubara
(74) *Attorney, Agent, or Firm* — David R. Crichton; Leo Kriksunov

(57) ABSTRACT

The present invention is directed to a flowable hemostatic paste comprising a crosslinked carboxymethyl cellulose and at least one non-toxic dispersant. More specifically the present invention relates to a hemostatic paste containing citric acid cross-linked CMC, which is suspended or dispersed as a powder in a mixture of a first non-toxic glycerol-containing hygroscopic dispersant and a second non-toxic alcohol functionalized dispersant comprising propylene glycol or 1,3-butanediol.

14 Claims, 11 Drawing Sheets

(51) Int. Cl.
*A61L 15/42* (2006.01)
*A61L 15/60* (2006.01)
*A61L 15/44* (2006.01)
*C08L 1/26* (2006.01)
*A61F 13/15* (2006.01)

(52) U.S. Cl.
CPC ............... *A61L 15/44* (2013.01); *A61L 15/60* (2013.01); *C08L 1/26* (2013.01); *A61F 2013/00523* (2013.01); *A61F 2013/15463* (2013.01); *A61L 2300/404* (2013.01); *A61L 2300/418* (2013.01); *A61L 2400/04* (2013.01)

(58) Field of Classification Search
CPC .......... A61L 15/42; A61L 24/08; A61L 15/44; A61L 2300/404; A61L 2300/418; A61L 2400/04; A61F 13/00063; A61F 13/00012; A61F 2013/15463; A61F 2013/00523; C08B 15/005
See application file for complete search history.

(56) References Cited

U.S. PATENT DOCUMENTS

| | | | |
|---|---|---|---|
| 4,002,173 | A | 1/1977 | Manning |
| 5,905,092 | A | 5/1999 | Osborne |
| 6,251,423 | B1 | 6/2001 | Bradford |
| 7,083,806 | B2 | 8/2006 | Rippon |
| 8,658,147 | B2 | 2/2014 | Sannino |
| 8,829,053 | B2 | 9/2014 | Salamone |
| 9,265,858 | B2 | 2/2016 | Larsen |
| 9,353,191 | B2 | 5/2016 | Sannino |
| 10,736,786 | B2 * | 8/2020 | Feng ................. A61F 13/00063 |
| 2002/0197302 | A1 | 12/2002 | Cochrum |
| 2004/0101548 | A1 | 5/2004 | Pendharkar |
| 2004/0142020 | A1 | 7/2004 | Jones |
| 2005/0037088 | A1 | 2/2005 | Pendharkar |
| 2005/0226916 | A1 | 10/2005 | Cochrum |
| 2005/0284809 | A1 | 12/2005 | Looney |
| 2007/0207180 | A1 | 9/2007 | Tanihara |
| 2007/0267439 | A1 | 11/2007 | Farzan |
| 2012/0070470 | A1 | 3/2012 | Pahari et al. |
| 2013/0089737 | A1 | 4/2013 | Sannino |
| 2013/0108682 | A1 | 5/2013 | Westrin |
| 2014/0105950 | A1 | 4/2014 | Hardy |
| 2015/0037314 | A1 * | 2/2015 | Larsen ................. A61K 9/1658 424/94.64 |
| 2016/0158407 | A1 * | 6/2016 | Larsen ................. A61L 24/104 424/94.64 |
| 2016/0206773 | A1 | 7/2016 | Mousa |
| 2017/0049850 | A1 | 2/2017 | Kuzma |

FOREIGN PATENT DOCUMENTS

| | | |
|---|---|---|
| CN | 101548733 A | 10/2009 |
| CN | 101932346 A | 12/2010 |
| CN | 101987207 A | 3/2011 |
| CN | 102379827 A | 3/2012 |
| CN | 104349797 A | 2/2015 |
| CN | 105025938 A | 11/2015 |
| CN | 105536039 A | 5/2016 |
| CN | 107754005 B | 6/2021 |
| DE | 10063827 A1 | 7/2002 |
| EP | 1493451 A1 | 1/2005 |
| EP | 1942117 A1 | 7/2008 |
| EP | 2532685 A1 | 12/2012 |

OTHER PUBLICATIONS

Capanema, et al., Superabsorbent crosslinked carboxymethyl cellulose-PEG hydrogels for potential wound dressing applications, International Journal of Biological Macromolecules, 2018, pp. 1218-1234, vol. 106.

Demitri, et al., Novel Superabsorbent Cellulose-Based Hydrogels Crosslinked with Citric Acid, Journal of Applied Polymer Science, Aug. 20, 2008, pp. 2453-2460, vol. 110.

Gosselin, et al., Determining Bulk Powder Particle Size through Texture Analysis, American Pharmaceutical Review, Feb. 25, 2013, pp. 1-9, Page Number.

International Search Report dated Dec. 20, 2019 for International Application No. PCT/IB19/56174.

Tian, A Clinical Observation On Treating Wound On the Face with Cataplasm of TCM, Journal of Henan University of Chinese Medicine, 2005, pp. 68-69, vol. 20, No. 5.

Zhang, et al., Research Progress in Renewable Natural Materials-based Green Superabsorbent Polymers, Materials Report, 2009, pp. 63-66, vol. 23, No. 17.

* cited by examiner

Hygroscopic paste | Paste with 10% water | Paste with 20% water

Hydrogel paste with 5% water, hard to be squeezed out from the tube

Hydrogel aste with 10% water filled into paste tube, turn into a rubber like material a few days later Spread paste on the matrix     Testing the adhesiveness on liver tissue

HEMOSTATIC PASTE AND METHODS OF MAKING THEREOF

CROSS REFERENCE TO RELATED APPLICATION

This application is a divisional of co-pending U.S. application Ser. No. 16/055,433 filed Aug. 6, 2018, which claims benefit of Chinese Patent Application Number CN 201810851056.6, filed Jul. 20, 2018, the complete disclosure of which is hereby incorporated herein by reference for all purposes.

FIELD OF THE INVENTION

The present invention relates generally to agents and materials for promoting hemostasis and tissue sealing and, more particularly, to fast swelling, highly absorbent hemostatic composition in a form of a paste comprising a mixture of crosslinked carboxymethyl cellulose with one or more dispersants, and to methods for manufacturing and using such hemostatic composition.

BACKGROUND

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances, substantial bleeding can occur. These situations usually require specialized equipment and materials as well as personnel trained to administer appropriate aid.

Bleeding during surgical procedures may manifest in many forms. It can be discrete or diffuse from a large surface area. It can be from large or small vessels, arterial (high pressure) or venous (low pressure) of high or low volume. It may be easily accessible or it may originate from difficult to access sites. The control of bleeding is essential and critical in surgical procedures to minimize blood loss, to reduce post-surgical complications, and to shorten the duration of the surgery in the operating room. The selection of appropriate methods or products for the control of bleeding is dependent upon many factors, which include but are not limited to bleeding severity, anatomical location of the source and the proximity of adjacent critical structures, whether the bleeding is from a discrete source or from a broader surface area, visibility and precise identification of the source and access to the source.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized.

To address the above-described problems, materials have been developed for controlling excessive bleeding or as adjuncts to hemostasis. Topical Absorbable Hemostats (TAHs) are widely used in surgical applications. TAHs encompass products in various forms, such as based on woven or non-woven fabrics or sponges, and are typically made of at least partially resorbable materials, ranging from natural to synthetic polymers and combinations thereof, including lactide-glycolide based co-polymers such as polyglactin 910, oxidized cellulose, oxidized regenerated cellulose (ORC), gelatin, collagen, chitin, chitosan, starch etc. Gelatin is used in various forms with or without a topical thrombin solution. Also, widely used are biologically active topical hemostatic products (topical thrombin solutions, fibrin sealants, etc.) and a variety of synthetic topical sealants.

To improve the hemostatic performance, scaffolds based on the above mentioned TAH materials can be combined with biologically-derived clotting factors, such as thrombin and fibrinogen.

Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. Many methods for forming various types of hemostats based on oxidized cellulose materials are known, whether made in powder, woven, non-woven, knit, and other forms. Currently utilized hemostatic wound dressings include knitted or non-woven fabrics comprising oxidized regenerated cellulose (ORC), which is oxidized cellulose with increased homogeneity of the cellulose fiber.

Fibrinogen and thrombin are critical proteins involved in achieving hemostasis after vascular injury and essential to blood clot formation. Fibrinogen and thrombin can be combined in powder form or in a non-aqueous suspension, without initiating a typical clotting reaction, thus preventing the formation of a fibrin clot until the proteins are hydrated in an aqueous medium or other liquid environment in which the proteins are soluble. An admixture of these proteins in powder form have a variety of potential biomedical applications including topical hemostasis, tissue repair, drug delivery, etc. In addition, an admixture of these proteins may be loaded onto a carrier or substrate, or other medical device, in powder form to form a product that may be used for example as a hemostatic device.

Fibrin sealants, also known as fibrin glue, have been in use in the clinic for decades. Oftentimes, fibrin sealant consists of two liquid components, a fibrinogen comprising component and a thrombin comprising component, which are stored frozen due to their inherent instability. Sometimes fibrin sealant products consist of two freeze dried components, which require reconstitution immediately prior to use and delivery by a conjoined syringe or other double-barreled delivery device. Freeze dried formulations are typically stable, but the fibrinogen component is difficult to reconstitute. Many hemostatic formulations currently available on the market or in development utilize lyophilized fibrinogen, frequently in combination with lyophilized thrombin, with hemostatic formulations applied in the form of dry powder, semi-liquid paste, liquid formulation, or optionally disposed on a supporting scaffold such as absorbable fabric scaffold.

To provide dressings with enhanced hemostatic and tissue sealing and adhering properties, therapeutic agents, including, but not limited to, thrombin, fibrin and fibrinogen have been combined with dressing carriers or substrates, including gelatin-based carriers, polysaccharide-based carriers, glycolic acid or lactic acid-based carriers and a collagen matrix.

U.S. Pat. No. 8,858,969, entitled Hemostatic compositions, devices, and methods, discloses a hemostatic device comprising: a container comprising a bottle, vial, canister, tube, or reservoir with an interior enclosure which contains a flowable hemostatic composition comprising a clay dispersed in an aqueous medium; wherein at least about 50% of the clay comprises particles with a particle size between about 1 nm and 10 μm; wherein the composition is a liquid which is substantially free of visible clay particles such that an appreciable amount of the clay particles does not settle from the liquid upon standing for at least about 12 hours; and wherein the composition is sterilized; and a dispensing component in fluid communication with the container; wherein the device is configured so that the dispensing component is capable of dispensing the hemostatic composition from the container directly to a bleeding area of an animal or person.

U.S. Patent Publication No. 2014/0369991, entitled Formulations for Wound Therapy discloses a pharmaceutical composition comprising an absorbable carrier of a biocompatible, biodegradable polymer and dispersed, at least partially through or on said absorbable carrier, microparticles comprising fibrinogen in an amount of from about 0.1-15 mg/cm$^2$ and/or microparticles comprising thrombin in an amount of from about 0.01 to 500 IU/cm$^2$, wherein the microparticles further comprise a glassy carrier.

U.S. Patent Publication No. 2016/0206773, entitled Composition and Method for Stopping Hemorrhage, Infection, and Accelerating Healing in Various Types of Wound or Burns discloses a composition, comprising: a hydrogel matrix comprising at least one polymer cross linked, via ionic or covalent bonding, with both hyaluronic acid and alginic acid, wherein the at least one polymer is selected from the group consisting of chitosan, poly L-Lysine, or a combination thereof.

U.S. Pat. No. 9,265,858, entitled Dry haemostatic composition discloses a method of preparing a dry composition suitable for use in haemostasis and wound healing, comprising the sequential steps of: a) providing a cross-linked biocompatible polymer in powder form, one or more polyols and an aqueous medium, wherein the one or more polyols are selected from sugar alcohols and sugars; b) mixing the biocompatible polymer, the one or more polyols and the aqueous medium to obtain a paste; and c) freeze-drying the paste to produce a dry composition, wherein the dry composition is capable of reconstituting to form a substantially homogeneous paste without mechanical mixing, wherein the dry composition comprises from 10% w/w to 60% w/w of one or more polyols.

U.S. Pat. No. 2,772,999, entitled Hemostatic surgical compositions and dressings discloses a surgical composition for coagulating blood containing a hemostatic amount, at least about 2%, of cellulose derivative of the group consisting of free acid cellulose glycolic acid ether and free acid cellulose hydroxypropionic acid ether having degree of substitution at least about 0.5, and degree of neutralization in the approximate range 0 to 60% but sufficiently low so that the free carboxyl content of the cellulose is at least 0.5 per glucose unit.

U.S. Patent Publication No. 2004/0101548, entitled Hemostatic wound dressing containing aldehyde-modified polysaccharide discloses a hemostatic wound dressing, comprising: a substrate for contacting a wound, said substrate comprising; a wound-contacting surface; and a biocompatible, aldehyde-modified polysaccharide, wherein said wound dressing is hemostatic.

European Publication No. EP1493451, entitled Hemostatic devices and methods of making same discloses a composition, comprising: biocompatible, oxidized cellulose particles having an average designated nominal particle size of from about 0.035 to about 4.35 mm; and a biocompatible, porous water-soluble or water-swellable polysaccharide binder component; wherein said composition is suitable for use in a hemostatic device.

U.S. Pat. No. 3,328,259, entitled Dressing for a wound containing a hemostatic agent and method of treating a wound discloses a dressing for a wound comprising a flexible body large enough to cover an open lesion as a dressing, said 40 body containing a water-soluble plasma-soluble cellulose derivative having hemostatic and film-forming properties and having the property of combining with the plasma in a wound to form with said plasma an artificial water-insoluble eschar, said cellulose derivative being present in integral non-discrete form in said body and in proportions to cause said body to be effective in coagulating the plasma issuing from a moist lesion to which the dressing is applied.

U.S. Patent Publication No. 2007/0207180, entitled Synthetic polypeptide-containing bioapplicable material and film-forming material discloses a bioapplicable material containing a polypeptide, wherein the polypeptide comprises a synthetic polypeptide having at least an amino acid sequence represented by the formula: Pro-Y-Gly, wherein Y represents Pro or Hyp, and forming a collagen-like structure.

U.S. Patent Publication No. 2012/0070470, entitled Hemostatic compositions, devices, and methods, discloses a blood-clotting agent comprising: a composition comprising clay dispersed in a liquid medium, wherein the clay is less than about 10% by weight of the composition; and wherein the composition including the liquid medium and clay has a viscosity of about 1000 cP or less.

U.S. Patent Publication No. 2002/0197302, entitled Hemostatic polymer useful for rapid blood coagulation and hemostasis discloses a method for arresting bleeding and inducing rapid blood coagulation and clot formation at a bleeding site, comprising applying a dry dressing comprising a matrix containing a hemostasis-promoting amount of a hemostatic agent which accelerates blood coagulation and clot formation at an interface between a wound surface and hemostatic zone to said bleeding site for a period of time sufficient to induce rapid blood coagulation at said site and removing the dressing after the blood at said bleeding site has clotted.

U.S. Patent Publication No. 2005/0226916, entitled Hemostatic polymer useful for Rapid blood coagulation and hemostasis discloses a method for promoting blood coagulation at a bleeding site in a mammal comprising applying to said bleeding site a composition comprising porous polymeric spheres and allowing said blood coagulation to occur at said bleeding site.

Chinese Patent Publication No. CN101001649A, entitled Haemostatic composition comprising hyaluronic acid discloses hemostatic composition, comprising a bioabsorbable material and hyaluronic acid (HA) or a derivative thereof.

U.S. Pat. No. 4,002,173, entitled A Diester crosslinked polyglucan hydrogels and reticulated sponges thereof relates to hydrogel compositions of diester crosslinked polyglucans and a process for their preparation.

Chinese Patent Application Publication No. CN102379827A Toothpaste containing denichine and preparation method thereof relates to a toothpaste that has CMC is one of its components.

U.S. Patent Publication No. 2005/0037088, entitled Process of making flowable hemostatic compositions and devices containing such compositions discloses a process for making a flowable hemostatic composition, comprising: introducing a volume of a biocompatible liquid into a mixing vessel equipped with a means for mixing said liquid, introducing a volume of a biocompatible gas into said volume of liquid while said means for mixing is operating under conditions effective to mix said liquid and said gas together to form a foam comprising a discontinuous gas phase comprising said gas substantially homogenously dispersed throughout a continuous liquid phase comprising said liquid, introducing into said foam an amount of solid particles of a biocompatible polymer suitable for use in hemostasis and which is substantially insoluble in said liquid; and mixing said foam and said solid particles together under conditions effective to form a substantially homogenous composition comprising said discontinuous gas phase and said particles substantially homogenously dispersed throughout said continuous liquid phase, wherein the ratio of said volume of liquid, said volume of gas and said amount of solid particles is effective to provide said substantially homogeneous composition with hemostatic properties, thereby forming said flowable hemostatic composition.

U.S. Patent Publication No. 2005/0284809, entitled Hemostatic compositions and devices, discloses a plurality of packed particles comprising interstitial pores having a pore volume and a median pore diameter effective to provide improved absorption of physiological fluids or an aqueous media into said interstitial pores when placed in contact therewith, compared to a plurality of unpacked particles of the same material, said particles comprising a biocompatible material and having a median diameter suitable for use in providing hemostasis to a site of a body of a mammal requiring hemostasis.

U.S. Pat. No. 7,083,806, entitled Wound gels, discloses a hydrogel comprising a pre-crosslinked gellant, water, and a poloxamer, wherein the concentration of said poloxamer is between 10 and 25% by weight of the hydrogel and the gellant comprises at least one cross-linked, superabsorbent polysaccharide, said hydrogel exhibiting thermally induced viscosification at a temperature between ambient and 35° C., and wherein said hydrogel has the capacity to absorb at least 50% further water in addition to the water already present, specifying water presence in the hydrogel.

European Publication No. 1942117A1, entitled Derivatives of acid polysaccharides discloses acid polysaccharides characterized by the concomitant presence of partial esters with non-polysaccharide carboxylic acids and esters between the acid groups of the initial polysaccharide and the alcohol groups of the repetitive units, with the formation of crosslinking between the polysaccharide chains.

U.S. Pat. No. 9,353,191, entitled Method for producing hydrogels, discloses a polymer hydrogel consisting essentially of carboxymethyl cellulose cross-linked with citric acid characterized by (a) a tapped density of at least 0.5 g/cm$^3$; and (b) a media uptake ratio in simulated gastric fluid/water (1:8) of at least about 50 at 37° C.

U.S. Pat. No. 8,658,147B2, Polymer hydrogels and methods of preparation thereof (also European Patent Publication No. EP2532685A1) discloses a method of treating obesity in a subject in need thereof, comprising the step of orally administering to the subject a therapeutically effective amount of a polymer hydrogel comprising carboxymethyl cellulose covalently cross-linked with citric acid.

U.S. Pat. No. 5,905,092, entitled Topical antibiotic composition providing optimal moisture environment for rapid wound healing that reduces skin contraction discloses a composition for the treatment of wounds comprising: a topical semisolid which is capable of providing a moist environment for a wound by promoting increased water content in wounds becoming dry and promoting reduced water content in wounds having excess exudate, comprising vehicles, which are capable of incorporating water to at least about 30% of their initial application weight, while also being capable of retaining at least about 70% of their application weight for two hours when left on a non-absorbing surface; an antibiotic formulation; and at least 60% by weight of water, wherein the topical semisolid comprises from about 10% to about 20% by weight of a polyhydric alcohol and from about 0.5% to about 10% by weight each of two or more gelling agents selected from the group consisting of hydroxyethyl cellulose, hydroxypropyl cellulose, polyvinylpyrrolidone, cross-linked acrylic acid polymer, PVM/MA decadiene crosspolymer and ammonium acrylates/acrylonitrogen.

U.S. Patent Publication No. 2013/0108682, entitled Wound Care Product Comprising a Cathelicidin Polypeptide, discloses a wound care product comprising a wound care material and a polypeptide having wound healing properties, wherein the polypeptide having wound healing properties is a cathelicidin, or a fragment, variant or fusion thereof which retains, at least in part, the wound healing activity of said cathelicidin.

U.S. Pat. No. 8,829,053, entitled Biocidal compositions and methods of using the same discloses an antimicrobial composition, comprising: at least one polymeric biguanide in an amount of at least 0.05 weight %, a chelating agent at a concentration of from 0.01 weight % to 1 weight %, and a vicinal diol component comprising at least one monoalkyl glycol and at least one monoalkyl glycerol, wherein a weight ratio of said at least one polymeric biguanide and said vicinal diol component ranges from 1:0.05 to 1:500, wherein said antimicrobial composition kills at least 99.99% of organisms in a biofilm within ten minutes of treatment with said antimicrobial composition.

U.S. Patent Publication No. 2014/0105950, entitled Haemostatic Material discloses a haemostatic material comprising a haemostat agent and a bioadhesive agent, wherein the haemostat agent is selected from the list consisting of: oxidised regenerated cellulose, kaolin, gelatin, calcium ions, zeolite, collagen, chitosan and chitosan derivatives.

An article "Novel Superabsorbent Cellulose-Based Hydrogels Crosslinked with Citric Acid" by Christian Demitri, et al., Journal of Applied Polymer Science, Vol. 110, 2453-2460 (2008) discloses the preparation of new environmentally friendly hydrogels derived from cellulose and hence originating from renewable resources and characterized by biodegradable properties. Two cellulose derivatives, sodium carboxymethyl cellulose (CMCNa) and hydroxyethyl cellulose (HEC), were used for superabsorbent hydrogel preparation. Citric acid (CA), a crosslinking agent able to overcome toxicity and costs associated with other crosslinking reagents, was selected in a heat activated reaction. Differential scanning calorimeter (DSC), Fourier transform infrared spectroscopy (FTIR), and swelling measurements were performed during the reaction progress to investigate the CA reactivity with each of the polymers. Also, CMCNa/HEC polymer mixtures (3/1 w/w) crosslinked with CA were investigated and compared with previous results.

There is a need in improved hemostatic forms and materials which facilitate ease of application and rapid onset of hemostasis.

SUMMARY OF THE INVENTION

The present invention is directed to a flowable hemostatic paste comprising a crosslinked carboxymethyl cellulose (CMC) and at least one non-toxic dispersant. Non-toxic means, for purposes of this application, a material that is generally regarded as safe according to one or more food and/or drug related regulatory agencies, though not limited only to such GRAS materials now or in the future and may include other materials sharing similar safety characteristics and suitability for human consumption. The hemostatic paste is absorbent, swellable, and biodegradable. CMC is preferably cross-linked by a polyfunctional carboxylic acid, wherein said acid is preferably selected from the group consisting of malic, tartaric, citric, malonic, succinic, glutaric, adipic acid and mixtures thereof.

In some embodiments, the hemostatic paste comprises 35% to 65% by weight of citric acid cross-linked CMC, which is suspended or dispersed as a powder in a mixture of a first non-toxic hygroscopic dispersant comprising glycerol, preferably a substantially pure 100% glycerol, in thick liquid format, pharmaceutical grade, and a second non-toxic dispersant comprising propylene glycol, 1,3-Butanediol or mixtures thereof.

In some embodiments cross-linked CMC comprises a powder having average particle size less than 100 microns and the paste is substantially free of water or is substantially anhydrous. In some embodiments, the paste further comprises a neutralizing alkaline agent.

According to some embodiments of the present invention, there is provided a method of making a flowable hemostatic paste comprising the steps of: cross-linking CMC by mixing CMC with citric acid in presence of water and reacting CMC with citric acid at elevated temperature; Drying the cross-linked CMC; Milling the cross-linked CMC to a powder having average particle size of less than 100 microns; Adding glycerol into the CMC powder, and mixing until a homogenous dough-like material is formed; Adding propylene glycol to said dough-like material and mixing thoroughly; Thus forming said flowable hemostatic paste.

According to some embodiments of the present invention, there is provided a method of using the hemostatic paste, comprising the steps of: applying the hemostatic paste, optionally supported on a flexible absorbable sheet substrate, onto or into a bleeding tissue or wound.

DETAILED DESCRIPTION

Figure 1:
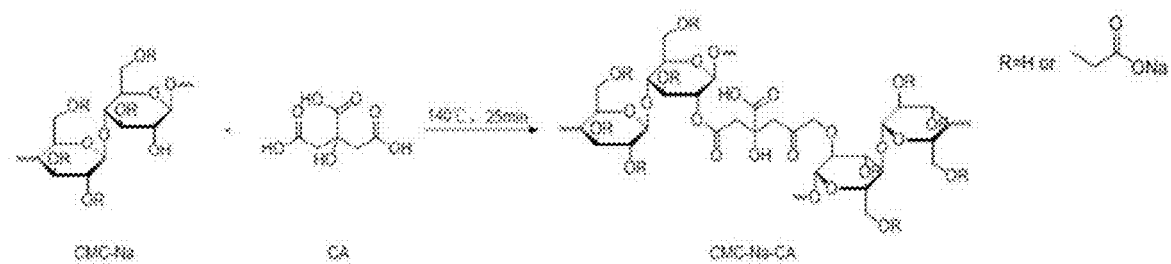
FIG. 1 shows schematic pathway for synthesis of cross-linked carboxymethyl cellulose (CMC).

The present invention relates generally to agents and materials for promoting hemostasis and tissue sealing and, more particularly, to fast swelling, highly absorbent hemostatic composition in a form of a paste comprising a mixture of crosslinked carboxymethyl cellulose with one or more dispersants, and to methods for manufacturing and using such hemostatic composition.

The embodiments of the present invention further relate to fast swelling, superabsorbable, biodegradable hemostatic paste. In some embodiments, the hemostatic paste comprises at least three components. The first component comprises a xerogel powder that is synthesized by crosslinking carboxymethyl cellulose (CMC) using polyfunctional carboxylic acids such as citric acid (alternatively malic, tartaric, citric, malonic, succinic, glutaric, adipic acid etc.). A xerogel is obtained when the liquid phase of a gel is removed by evaporation. It typically exhibits shrinkage of greater than (>) 90%.

Cross-linked CMC can form hydrogel when placed in contact with body fluids. A hydrogel is a network of polymer chains that are hydrophilic, sometimes found as a colloidal gel in which water is the dispersion medium. The concentration of crosslinked CMC in the hemostatic paste ranges from about 35% to 65% weight by weight. The second component comprises a glycerol-containing dispersant at 10% to 30% weight by weight. The third component comprises an alcohol-functionalized dispersing agent at 10% to about 30% weight by weight, such as propylene glycol or 1,3-Butanediol. The hemostatic paste is biocompatible to treat mild or moderate bleeding.

According to one embodiment, a fast swelling, superabsorbable, biodegradable hemostatic paste comprises: carboxymethyl cellulose crosslinked by citric acid (or similar polyfunctional carboxylic acid e.g. malic, tartaric, citric, malonic, succinic, glutaric, adipic acid) 35% to 65% which is suspended or dispersed as a fine powder, as demonstrated in the examples, in a mixture of a first non-toxic glycerol-containing, hygroscopic dispersant and a second non-toxic alcohol-functionalized dispersant, preferably comprising propylene glycol or 1,3-Butanediol. A paste means, for purposes of this application, a flowable material that has sufficient viscosity and cohesion to maintain a continuous, singular form at room temperature when placed upon a flat, unconstrained flat surface. A pile of sand or similar collection of particulates would not be a paste as the individual particles lack sufficient cohesion with one another. The inventive formulation is substantially free of water or anhydrous. In some embodiments, both dispersants are hydrophilic.

Dried cross-linked CMC xerogel has three-dimensional crosslinked polymeric network that are capable of absorbing large quantities of water, saline or physiological liquid forming hydrogels. The powerful osmotic action dehydrates and gels the blood upon contact and swelling to more than 20 times of the dry xerogel volume to fill up a wound and produce a "back pressure" in the confined wound space to simulate tamponade effect and enhance the natural clotting process. The flowability and flexibility of the inventive paste also ensure its access to narrow spaces and its application to uneven surfaces, making it a useful material to address the intra-operational bleeding or oozing. The instant paste is particularly suitable for hard to access wounds such as tissue crevice or cavity bleeding.

In an alternative embodiment, the inventive paste can also be used in conjunction with a backing, pad, scaffold, or matrix to provide mechanical strength to cover the wound surface. In this case, the instant paste is supported on a pad for ease of application or tamponade.

In another embodiment, the instant hemostatic paste can be employed for a timed or delayed release of active agents e.g. as a drug-delivery vehicle. The composition can incorporate growth factors, antibiotics, local anesthetics, and any agents useful to improve wound healing, prevent infection or relieve pain. By incorporating coagulation activators, platelet activators or blood vessel constrictors, fibrinolytic function inhibitors, etc., including thrombin, fibrinogen, etc., the hemostatic effect of the paste could be further improved.

According to the inventive embodiments, the instant hemostatic paste is anhydrous and hygroscopic. It can absorb liquid, such as water, blood, etc., and expands to form hydrogel within seconds, such as within 5, 20, 30, 50, 120, 300 seconds, more preferably within 5-30 seconds.

The xerogel powder particles are suspended in dispersant components of the hemostatic paste. The resulting paste is flowable, and can be deposited into/onto uneven surfaces or into narrow spaces.

The main component of the paste forming the xerogel, is carboxymethyl cellulose, crosslinked by citric acid, resulting in an increased mechanical stability. Several polysaccharides show a high absorption ability in the unmodified state, but these have the disadvantage that the swelling occurs only in warm water and that dissolution can take place. Such unmodified/uncross-linked polysaccharides have low mechanical stability and can undergo degradation, and/or retrogradation, and/or and syneresis (contraction of a gel accompanied by the separating out of liquid).

The inventors observed that advantageously cross-linked CMC particles do not absorb the dispersants which are anhydrous but hydrophilic, glycerol and propylene glycol, despite glycerol and propylene glycol being hydrophilic, while particles were still capable to rapidly absorbing blood, plasma, water, bodily fluids.

Without wishing to be bound by any theory, the non-aqueous solvents/carriers/dispersants are outside of the crosslinked network particles and should not influence their ability to absorb liquids. The absorption would appear to be maximized by eliminating pre-swelling or pre-load. The particles do not swell or absorb the selected solvents/carriers/dispersants but can quickly swell when provided with plasma and absorb the greatest % of plasma components. Presence of compounds such as sorbitol in the cross-linking reaction solution may result in the sorbitol would become entrapped within the cross-linked network. The entrapped sorbitol would then help to prevent excessive crosslinking by taking up space for a network link and could also alter the hydrophilicity of the overall particle by attracting water into the crosslinked particles. Thus, it is preferred that the present system is devoid of sorbitol or similar chemical moieties and/or excipients. The selected solvents/carriers/dispersants should not shield the crosslinked network particles from the plasma components that are intended to be absorbed.

Example 1. Making of the Hemostatic Paste and Paste Composition

Referring to FIG. 1, one schematic pathway for synthesis of cross-linked carboxymethyl cellulose (CMC) is shown, with initial reagents being CMC sodium salt (CMC-Na) and Citric acid (CA), with the reaction carried out, as an example only, at 140° C. for 25 min, resulting in the cross-linked CMC (CMC-Na-CA). Dried cross-linked CMC, which can be referred to as a xerogel or dried, compact hydrogel, is then used as a component for forming the inventive highly absorbent (super absorbent) hemostatic paste.

In one embodiment, CMC was cross-linked by citric acid as follows. The sodium salt of the CMC (supplier: Shanghai Aladdin biochemical Technologies Co. Ltd, China) was used for the synthesis of the hydrogels. A cross-linker ratio Fz of 0.025 was used. Fz is defined as the amount of cross-linking agent divided by the amount of anhydroglucose units. The cross-linking agent was first dissolved in distilled water and then thoroughly homogenized with the CMC, resulting in a homogeneous dough-like product. The dough-like product was then chopped into small chunks. The product was heated at 140° C. for 25 min in a preheated oven to accomplish cross-linking. The obtained product was dried at 70□ overnight and then ground to an average particle size of below 100 μm.

The resulting cross-linked CMC powder was then mixed with dispersants as follows. Glycerol (in some embodiment containing 1% of NaOH) was added into powder, and mixed/stirred until all powder particles are coated by glycerol, forming a dough-like paste. Then propylene glycol is added to the above paste, and mixed/stirred, to form the final, flowable hemostatic paste.

Sodium hydroxide is added into glycerol to neutralize the free acid. Sodium hydroxide component is believed to chemically stabilize the formulation by neutralizing the unreacted citric acid and polycarboxylic group of the carboxymethyl cellulose. Undesirably, the carboxylic group in the citric acid and the crosslinked CMC might react with the hydroxyl group in the propylene glycol resulting in an esterification reaction which may cause the hardening of the paste over time. Sodium hydroxide further is expected to improve the water absorption and swelling property of the cross linked carboxymethyl cellulose.

According to one embodiment, glycerol was used with about 1% of sodium hydroxide dissolved in it to adjust pH. NaOH was added to glycerol at elevated temperature, such as 65° C., resulting in rapid dissolution and no precipitating out upon cooling to ambient temperature of 20-25° C. The pH of the glycerol was measured as 5.7 with NaOH added, prior to adding NaOH pH was 5.18.

Without wishing to be bound by any theory, additions of sodium hydroxide enable improved performance and stability of the final hemostatic paste. The —COOH group in the CMC-CA may tend to react with —OH group of propylene glycol and cause limited stability of the paste. Use of NaOH then enables formulation which has the —COOH groups at least partially neutralized. However simply adding NaOH into the CMC-CA paste will not be practical or possible because with such small amount of NaOH powder, it is virtually impossible to uniformly and homogenously disperse it through the CMC-CA powder matrix. On the other hand, dissolving NaOH in water and then adding it as aqueous solution also will not work as the paste formulation needs to be anhydrous. Even small quantities of water present in contact with the CMC-CA powder could cause the powder to swell and may compromise the ability to quickly absorb blood when applied to the wound.

Advantageously, for the inventive hemostatic paste, the dispersant is anhydrous. According to embodiments of the present invention, for the dispersant selection, the key requirements are non-toxic, anhydrous, able to dissolve NaOH, and biocompatible. While NaOH was found to be very poorly soluble at room temperature in glycerol (i.e. it was exceedingly difficult to dissolve NaOH at room temperature) the inventors discovered that NaOH can be easily dissolved in glycerol at about 65° C. and then will not precipitate upon cooling. Table 1 shows the solubility of NaOH in glycerol as a function of temperature. Full dissolution was observed at least 65° C.

TABLE 1

Dissolution temperature of NaOH in glycerol
100 mg of NaOH powder mixing with 10 g of glycerol

| Temperature ° C. | Dissolving or not |
|---|---|
| 25 | no |
| 35 | no |
| 45 | no |
| 55 | no |
| 65 | yes |

After dissolving 1% of NaOH in glycerol, the inventors used this solution to partially neutralize the formulation, improve stability and swellability. As discussed above, pH was adjusted from 5.18 to 5.71.

Referring to Table 2, Composition of hemostatic paste is presented. All components are biocompatible.

TABLE 2

Composition of the hemostatic paste

| Compound | Function | Weight % concentration | Weight to prepare 10 g of paste, g |
|---|---|---|---|
| Cross-linked CMC powder (CMC-CA) | Absorbent particles | 53.1% | 5.31 |
| 1% NaOH in glycerol | Dispersant | 26.5% | 2.65 |
| Propylene glycol | Dispersant | 20.4% | 2.04 |
| TOTAL: | | 100 | 10 g |

Figure 2:
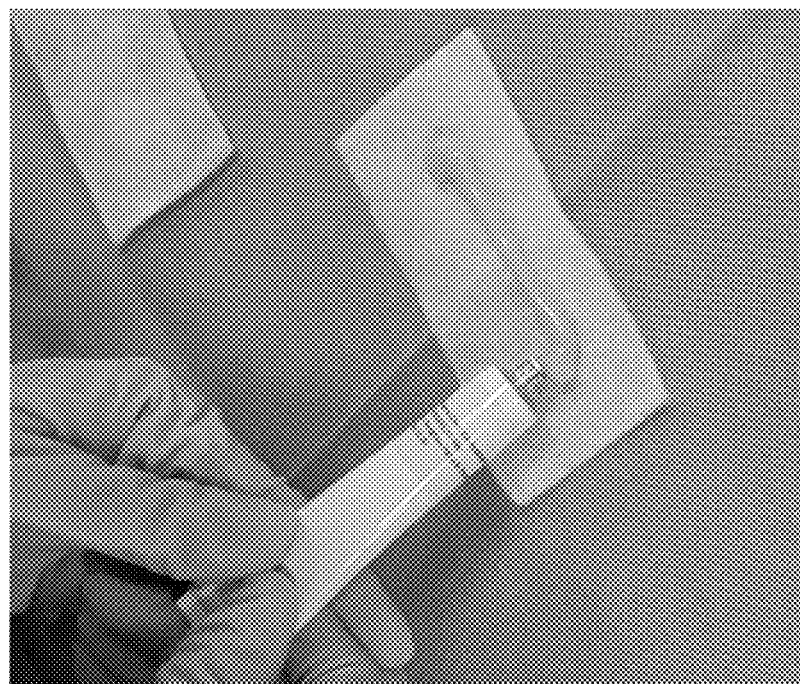
FIG. 2 is a photo showing hemostatic paste as it is expressed from a tube onto a substrate.

Referring to FIG. 2, appearance of the inventive hemostatic paste is shown as it is expressed from a tube onto a substrate. The paste is anhydrous, flowable and ready-to-use. It can be used by directly applying it to a bleeding site, or be used together with a hemostatic gauze or substrate, absorbable or not absorbable.

Comparisons of hemostatic paste with only one dispersant to the instant hemostatic paste are presented below. Hemostatic paste formulated with glycerol only, without the second dispersant (such as propylene glycol or 1,3-Butanediol), will have very high viscosity and the composition with only glycerol has poor absorbing properties. Hemostatic paste formulated with the second dispersant propylene glycol or 1,3-Butanediol, without the first dispersant (glycerol) would result in a poor dispersing effect of crosslinked CMC. Precipitation was observed within short time. However, Propylene glycol, as a water-miscible co-solvent, does not inhibit the crosslinked CMC from rapidly absorbing liquid. With both glycerol and the propylene glycol in a certain range, the viscosity of the paste can be tuned to ranges convenient for expressing and storage while no precipitation was observed, while at the same time properties of crosslinked CMC of rapidly absorbing liquids was maintained. Thus, it was shown that the presence of two dispersants, as described, was critical for the hemostatic paste handling, storage, and performance.

Advantageously, the present hemostatic paste compositions are anhydrous, with the water absence critical to performance.

Example 2. Swelling Properties of Cross-Linked CMC and Other Polysaccharides

For swelling testing, 1 gram of xerogel was immersed in excess DI water, saline or porcine plasma at room temperature for certain period to reach swelling equilibrium. At time intervals of 1, 2.5 min, swollen samples were separated from the unabsorbed DI water, saline or plasma by filtering through a 100-mesh screen. Swelling percent at each time point was calculated using the following formula Equation: $SP=100 (Mt-Md)/Md$ where SP is the swelling percent, Mt and Md are the weights of swollen hydrogel particles at time t and dry xerogel particles, respectively.

Figure 3:
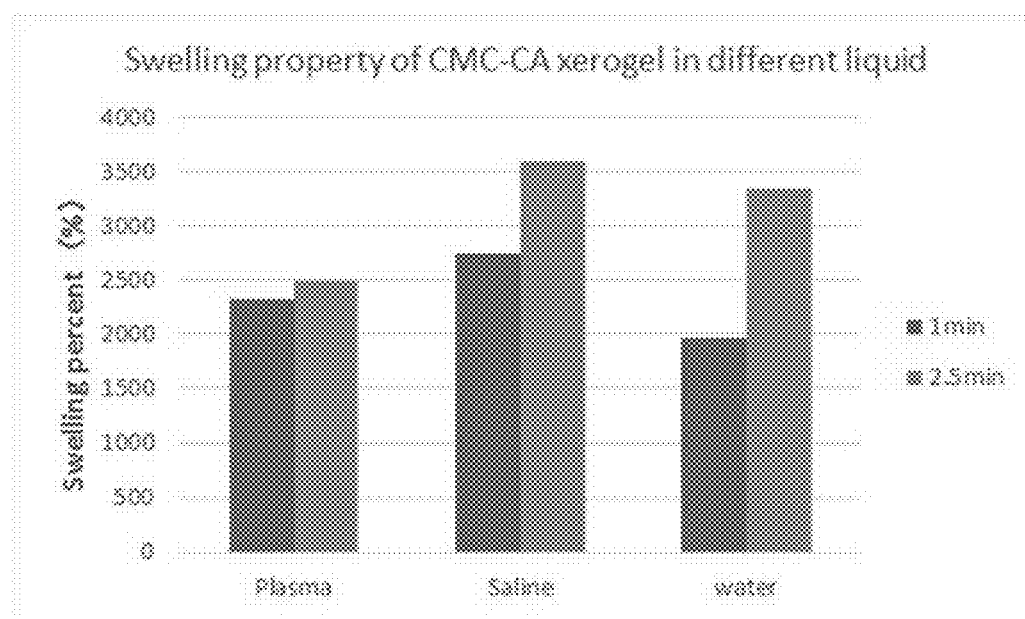
FIG. 3 shows swelling of CMC-CA xerogels in plasma, saline, and water at 1 min and 2.5 min after immersion.

Referring to FIG. 3, swelling of CMC-CA xerogels is shown in plasma, saline, and water at 1 min and 2.5 min after immersion, with significant swelling of the order of 1900-2700% at 1 min and 2500-3600% at 2.5 min observed experimentally.

Figure 4:
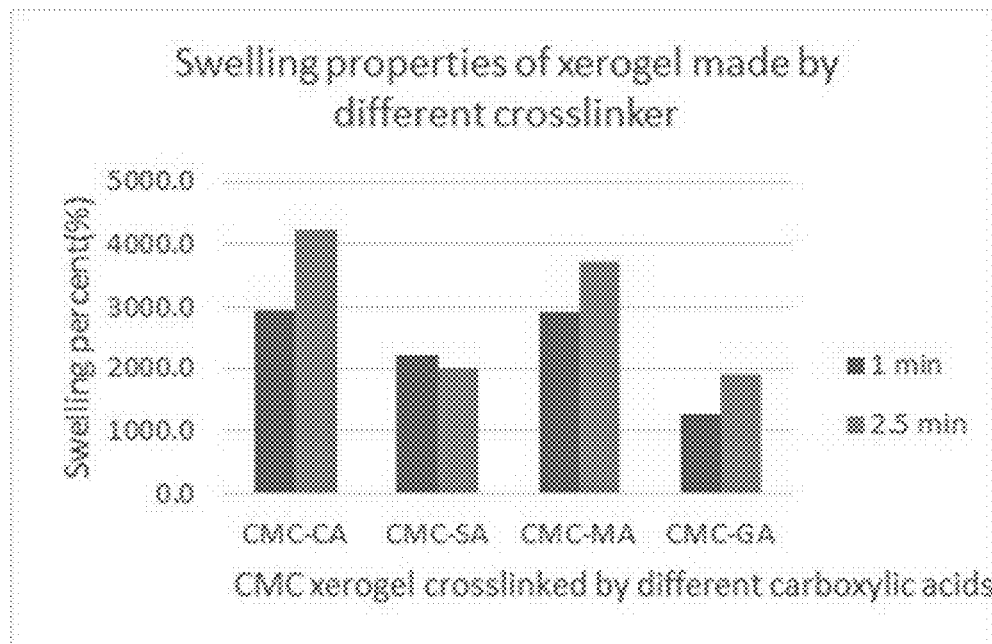
FIG. 4 shows swelling of CMC based xerogels cross-linked by different carboxylic acids upon exposure to water at 1 min and 2.5 min after immersion.

Referring to FIG. 4, swelling of CMC based xerogels crosslinked by different carboxylic acids is compared upon exposure to water at 1 min and 2.5 min after immersion. The data show that xerogels made by crosslinking CMC with Citric acid (CMC-CA) has strongest swelling capacity with significant swelling of the order of 2900% at 1 min and 4200% at 2.5 min observed experimentally, vs. somewhat lower swelling for xerogels made by crosslinking CMC with Succinic acid, Malic acid or Glutaric acid (CA: Citric acid; MA: Malic acid; SA: Succinic acid; GA: Glutaric acid).

Figure 5:
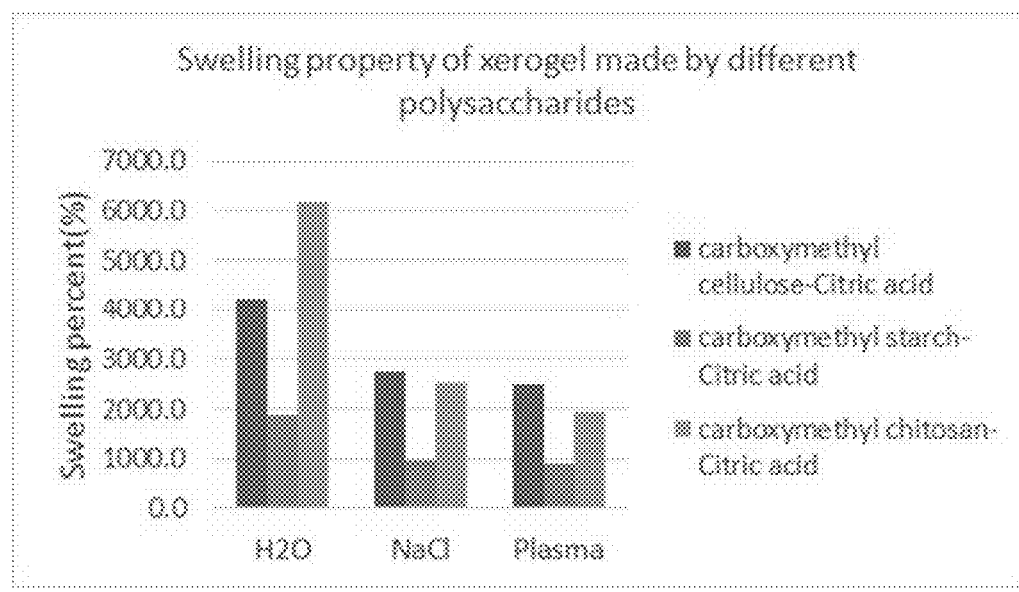
FIG. 5 shows swelling of xerogels made by crosslinking of different polysaccharides by citric acid in comparative chart for swelling in DI water, saline or porcine plasma.

Referring to FIG. 5, swelling of xerogels made by crosslinking of different polysaccharides by citric acid is presented in a comparative chart for swelling in DI water, saline or porcine plasma. As can be seen from the data presented, in water, xerogels made from carboxymethyl chitosan showed highest swelling property. However, in saline and plasma, xerogel made from carboxymethyl cellulose showed highest swelling property.

Example 3. Criticality of Water Absence

Figure 6:
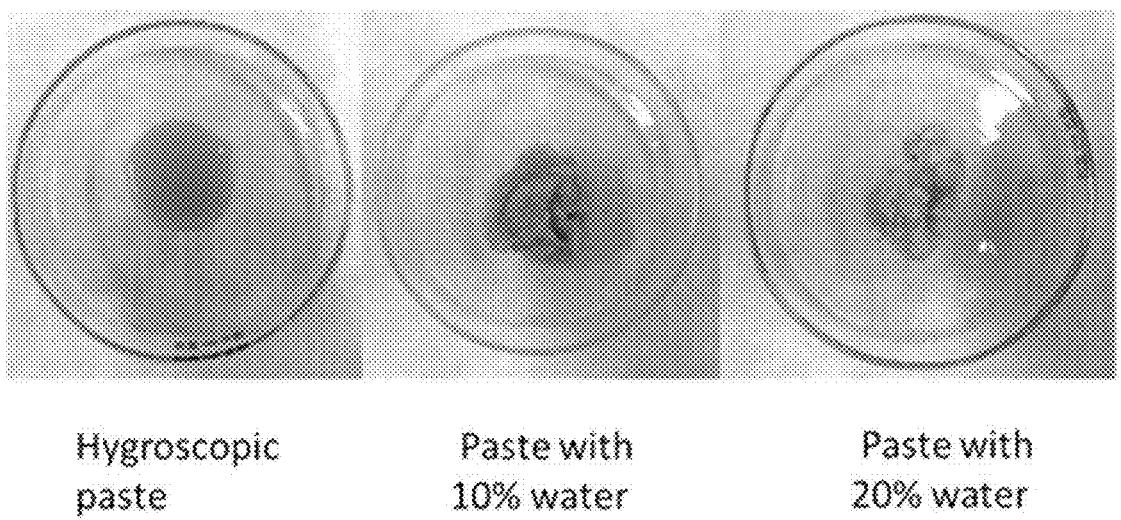
FIG. 6 shows hygroscopic or water-free paste relative to paste containing 10% and 20% water.

The criticality of water absence was further evaluated by testing the instant hemostatic paste with additions of water. It was shown that at 5% and above concentration of water, properties of the hemostatic paste have degraded. Referring to FIG. 6, hygroscopic or water-free paste is shown as flowable, semi-liquid material, while paste containing 10%, 20% water is shown as clumped, crumbly material.

Figure 7:
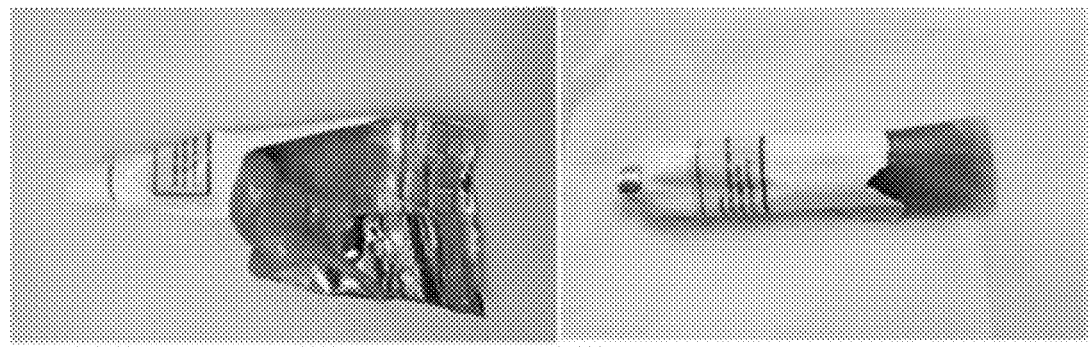
FIG. 7 shows the hydrogel paste containing 5% and 10% of water in a cut open dispensing tube.

Referring to FIG. 7, The flowability of the hydrogel paste is reduced when containing water, potentially due to volume expanding of hydrogel particles, especially over time. The paste containing 5% of water is shown in a cut open dispensing tube, with properties making it hard to dispense. The paste containing 10% water is shown as rubber-like solidified material which will not be possible to express from the tube.

Thus, the water content can compromise the flowability of the instant hemostatic paste with the water content is inversely proportional to the flowability of the paste. Thus, it is preferred that the paste is substantially water free, or has water content 0-5%, such as 0, 0.5, 1, 2, 3, 5%.

Example 4. Evaluations of Optimal Concentration Ranges and Optimal Ratios

A range of different formulations of the hemostatic paste was further evaluated. Referring now to Table 3, several formulations of the hemostatic paste are presented, with all having 53% by weight CMC-CA and variable amounts of glycerol, propylene glycol (PG) dispersants.

TABLE 3

Formulations of hydrogel paste

| | CMC-CA/g | propylene glycol/g | glycerol/g | CMC % | PG % | Glycerol % | Formulation description |
|---|---|---|---|---|---|---|---|
| 1 | 5 | 0.00 | 4.44 | 53% | 0.0% | 47% | Only Glycerol |
| 2 | 5 | 2.22 | 2.22 | 53% | 24 | 24 | PG:Glycerol 1:1 |
| 3 | 5 | 1.78 | 2.66 | 53% | 19 | 28 | PG:Glycerol 1:1.5 |
| 4 | 5 | 1.48 | 2.96 | 53% | 16 | 31 | PG:Glycerol 1:2 |
| 5 | 5 | 1.92 | 2.52 | 53% | 20 | 27 | PG:Glycerol 1:1.3 |
| 6 | 5 | 4.44 | 0.00 | 53% | 47 | 0.0 | Only PG |
| 7 | 5 | 2.66 | 1.78 | 53% | 28 | 19 | PG:Glycerol 1.5:1 |
| 8 | 5 | 2.98 | 1.48 | 53% | 32 | 16 | PG:Glycerol 2:1 |

Figure 8:
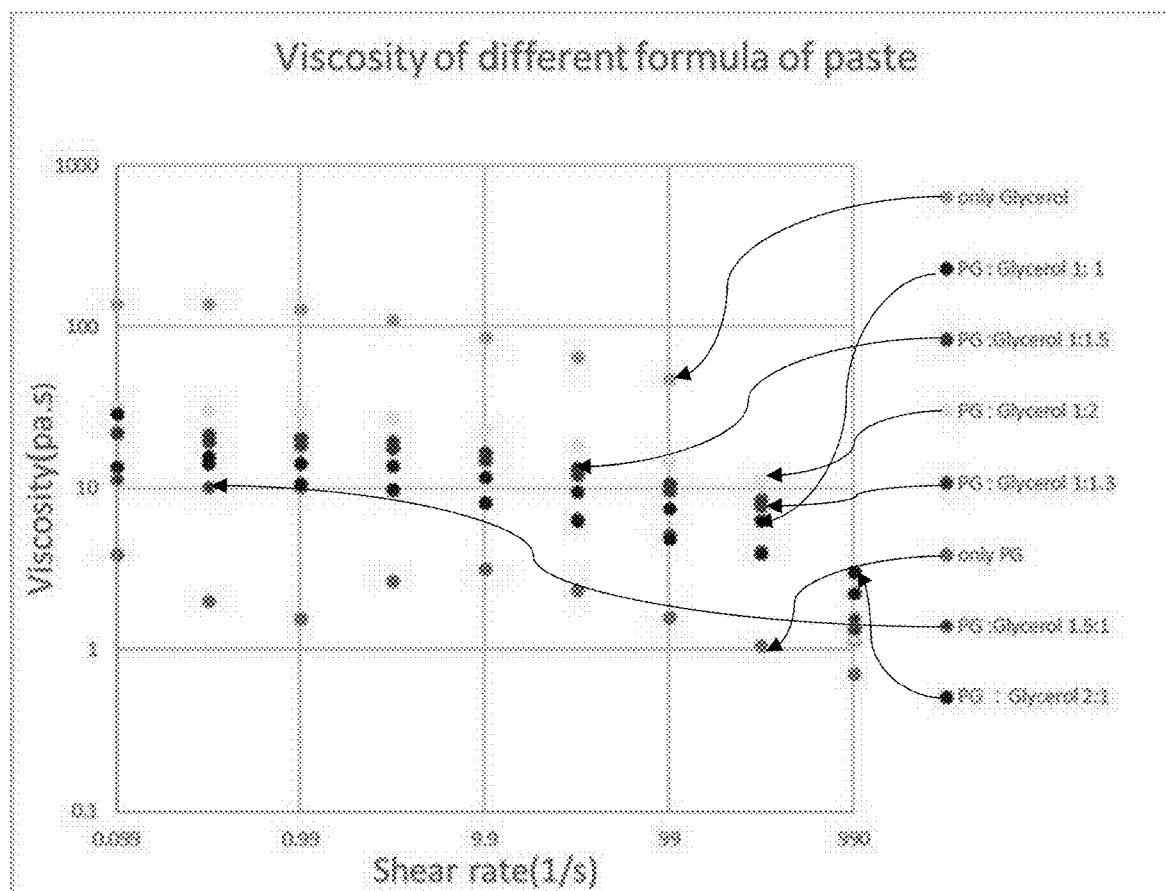
FIG. 8 shows a chart presenting viscosities of different formulations of the instant hemostatic paste as a function of shear rate.

Referring to FIG. 8, viscosities of different formulations of the instant hemostatic paste are presented as a function of shear rate. The data was measured by Discovery HR-3 hybrid rheometer (TA instruments), using flat plate, steady shear test. It was discovered that for a hemostatic paste with good performance, the viscosity should rapidly decrease while the shear force is increasing, corresponding to ease of expressing the paste from the storage container when being applied. The paste should also have high viscosity at stationary state, which makes it stay at where it is applied instead of flowing away (run-off). Eight different formulations were tested to evaluate the appropriate range of the dispersants. According to the viscosity data and the performance of paste on the animal tissue, the range between PG-glycerol 1:0.5 to PG-glycerol 1:2 is the best performing range. Referring to Table 3, showing eight different formulations tested, for 100 g of paste, the CMC powder represents 53% (w/w) of the total weight and that of Glycerol is between 16%-31% (w/w).

A range of compositions with variable ratios of glycerol and propylene glycol were further evaluated and optimized. Referring to Table 4, properties of the resulting hemostatic paste are shown as a function of the composition.

TABLE 4

Glycerol and the propylene glycol ratio optimization.

| | CMC-CA, g | Propylene Glycol (PG), g | Glycerol, g | CMC-CA % | PG % | Glycerol % | glycerol/PG RATIO | CMC-CA/glycerol RATIO | Appearance/flowability/viscosity of paste |
|---|---|---|---|---|---|---|---|---|---|
| 1 | 8.4 | 6.3 | 0 | 57 | 43 | 0 | 0 | 1.33 | "thin" |
| 2 | 5.76 | 2.3 | 4.3 | 47 | 17 | 35 | 1.87 | 0.87 | "Thick" |
| 3 | 13 | 5 | 6.55 | 53 | 20 | 27 | 1.31 | 1.13 | "moderate" |
| scale up | 61.26 | 23.5 | 30.62 | 53 | 20 | 27 | 1.30 | 1.13 | "Moderate" |

The terms "Thick", "Thin", "Moderate" above are based on flowability and appearance. The "thick" sample is almost un-flowable, and will not conform well to the irregular shape of wound site. The "thin" sample is too liquid resulting in easy to runoff and not staying in place. "Moderate" compositions were found to be acceptable in that they can be easily shaped, conformed well to the wound site, and resulted in no runoff.

Compositions containing about 49-55% of CMC-CA are preferred.

Compositions containing about 18-30% of glycerol are preferred.

Compositions containing about 15-30% of propylene glycol are preferred.

Compositions characterized by the ratio of glycerol to propylene glycol (by weight) of about 1-1.5 are preferred.

Compositions characterized by the ratio of CMC-CA to glycerol (by weight) of 0.9-1.25 are preferred.

Example 5. Dispersants Comparisons

In some embodiments, three different dispersants were compared: propylene glycol, dipropylene glycol, 1,3-Butanediol, as shown in Table 5. At the same ratio, the dipropylene glycol paste is stickier and less useable than the other two. The flowability of the dipropylene glycol paste was not as good as paste formulated with propylene glycol and the 1,3-Butanediol.

TABLE 5

Dispersants comparisons

| | Actual weight/g |
|---|---|
| CMC-CA | 5.31 |
| glycerol | 2.94 |
| propylene glycol | 2.28 |
| RESULT: Paste with moderate viscosity, acceptable flowability | |
| CMC-CA | 5.31 |
| glycerol | 2.94 |
| dipropylene glycol | 2.31 |
| RESULT: Paste with sticky viscosity, not acceptable | |
| CMC-CA | 5.31 |
| glycerol | 3.04 |
| 1,3-Butanediol | 2.3 |
| RESULT: Paste with moderate viscosity, acceptable flowability | |

Example 6. Paste-Powder Comparisons

Figure 9:
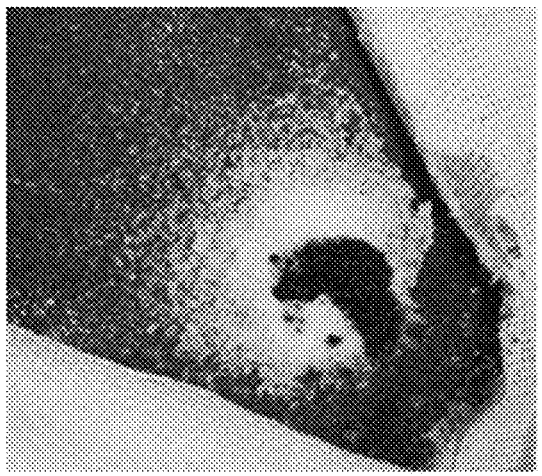
FIG. 9 is showing CMC-CA powder on animal model bleeding site comprising a puncture wound.
Figure 10:
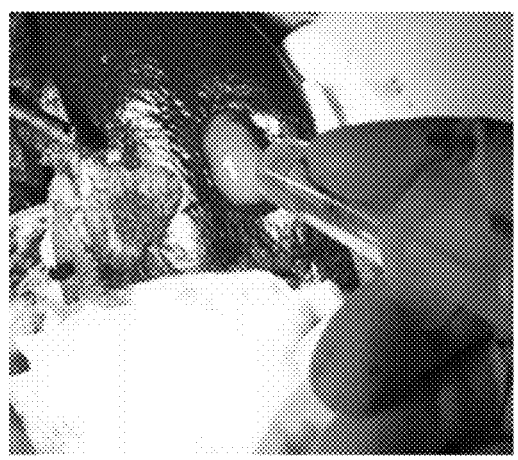
FIG. 10 is showing the hemostatic paste precisely delivered to the wound site.
Figure 11:
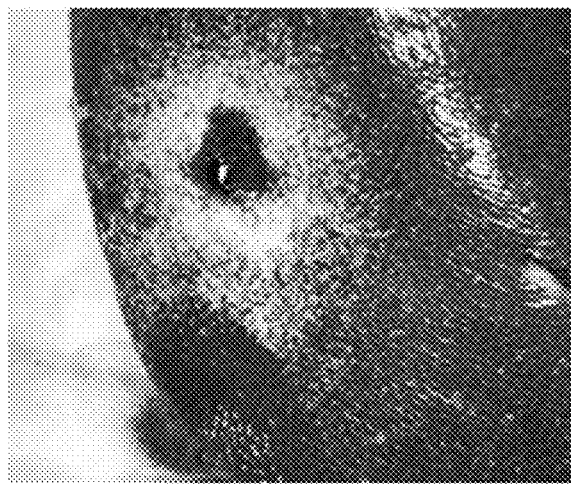
FIG. 11 is showing CMC-CA powder applied on the puncture model.

CMC-CA powder was further compared to the inventive paste in performance, and the advantages in performance demonstrated showing that the flowable viscous paste format has advantages over the same material as a powder. According to an animal study result, although CMC-CA powder was also effective stopping bleeding in a puncture model, powder has exhibited two disadvantages comparing with the paste:

Powder was not possible precisely deliver, and as it was sprayed, the covering range was somewhat wide, not as suitable for a confined wound space. Referring to FIG. 9, showing CMC-CA powder on animal model bleeding site comprising a puncture wound, CMC-CA powder covers a wide surface area surrounding the puncture wound, resulting in broad coverage but lack of precise delivery. Referring to FIG. 10, showing the instant hemostatic paste delivery, paste is shown to be precisely delivered to the wound site, and does not block the vision. Referring to FIG. 11, CMC-CA powder applied on the puncture model shows less cohesiveness between particles and blood can break through the gaps between the powder particles.

Figure 12:
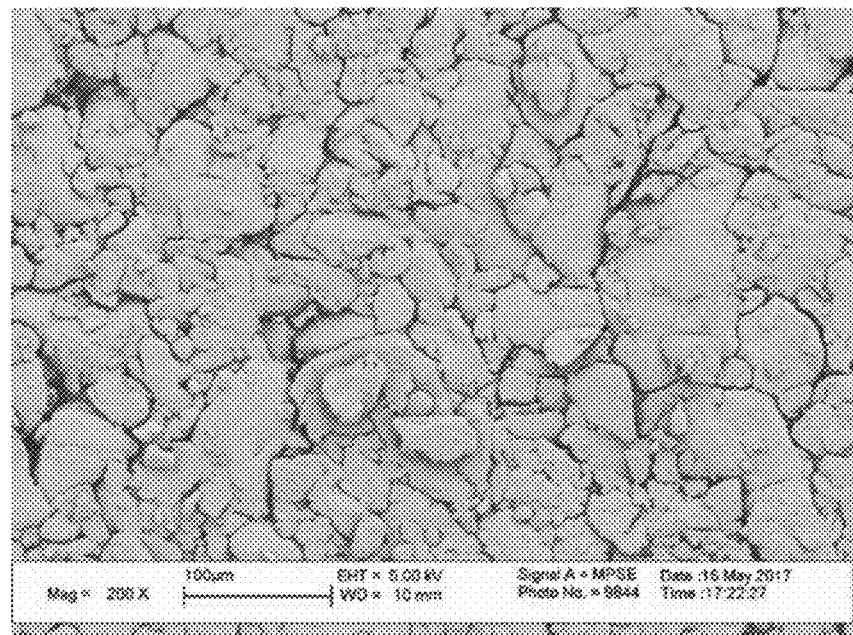
FIG. 12 is showing SEM micrograph of CMC-CA powder formed hydrogel

Referring to FIG. 12, SEM micrograph of CMC-CA powder (<100 μm) formed hydrogel is presented. The hydrogel formed by powder shows that there are still gaps, crevices within the hydrogel matrix. Through which blood can seep through or leak through.

Figure 13:
FIG. 13 is showing the inventive hemostatic paste applied onto the liver puncture model

Referring to FIG. 13, the inventive hemostatic paste is shown applied onto the liver puncture model, resulting in hemostasis. Paste format has higher cohesiveness among the particles compared with powders. No blood break-through through the paste was observed.

Example 7. CMC-CA Xerogel Particulate Properties

Figure 14:
FIG. 14 is showing the expressed hemostatic paste containing particle size 100 μm 300 μm.

CMC-CA powder with particle size 100 μm~300 μm was observed to result in solid powder in the paste started to precipitate during storage. When tube contained the hemostatic paste was squeezed to dispense the paste, dispersants came out first, and the powder settled to the bottom of the tube, and was hard to dispense, rendering a portion of the paste dry and non-flowable. However, powder particle size <100 μm such detrimental performance was not observed, with the paste kept homogeneous throughout storage, and none or minimal sedimentation was observed. Referring to FIG. 14, particle size 100 μm~300 μm is seen rendering a portion of the paste dry and non-flowable, due to precipitation.

Figure 15:
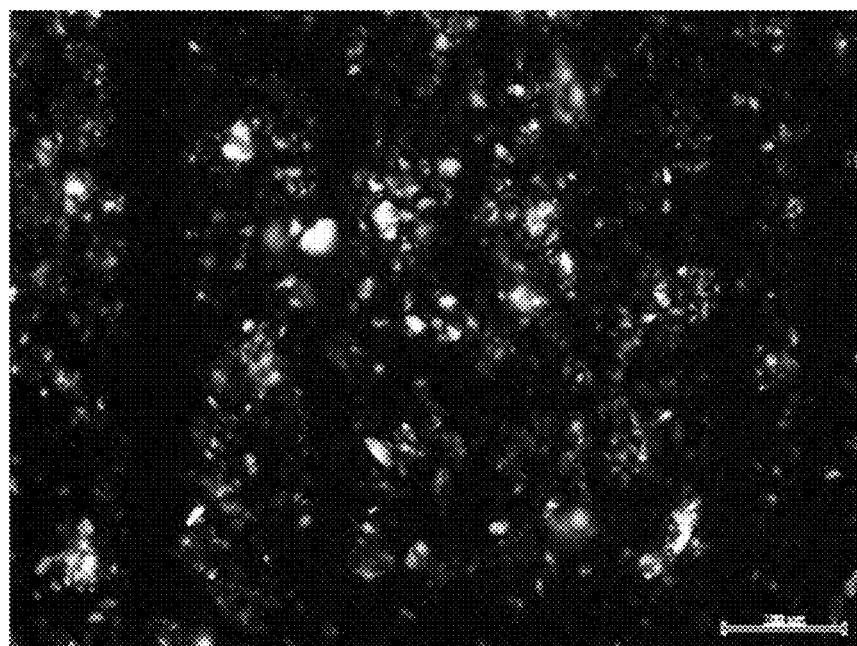
FIG. 15 is showing a micrograph of CMC-CA xerogel powder for particle size <100 μm.

CMC-CA powder was further characterized showing the shape of the particles is irregular, because of blender used to mill the powder. Referring to FIG. 15, Micrograph of CMC-CA xerogel powder is shown for particle size <100 μm.

Example 8. Hemostatic Paste Properties in Heparinized Animal Model: Hemostasis Data for Cross-Linked and Non-Cross-Linked CMC The hemostatic paste formulated as described in Example 1 was further evaluated in heparinized liver punch model (porcine), comparing paste formulated with citric acid cross-linked CMC (CMC-CA) and non-cross-linked CMC. The testing was performed as follows in heparinized animals. The animal (pig) was injected with heparin to inhibit the blood coagulation system. An 8-mm punch hole wound was made on the liver. The evaluated hemostatic paste was then applied into the punch hole wound and pressed with gauze for 1 minute. The gauze was removed to observe whether hemostasis is achieved. Extend the observation time up to 30 minutes to evaluate the effectiveness of the hemostatic paste.

Figure 16:
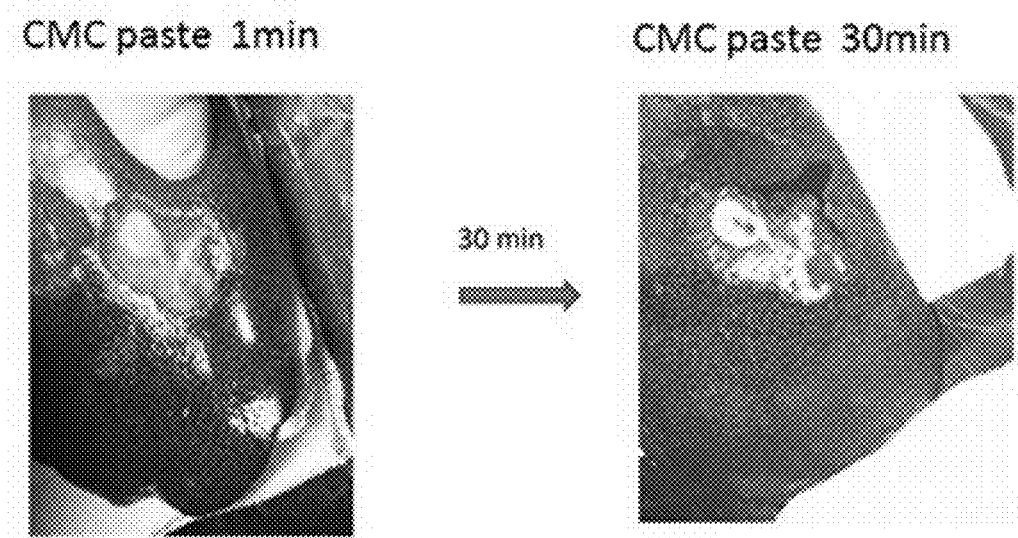
FIG. 16 shows the testing results of the hemostatic paste containing non-cross-linked CMC (comparative example).

Referring to FIG. 16, the testing results of the hemostatic paste formulated as described in Example 1, but using non-cross-linked CMC, is presented (comparative example). Non-crosslinked CMC hemostatic paste was applied into the punch wound, and hemostasis was achieved in 1 minute, as shown. However, re-bleeding was observed at around 30 minutes, as shown. Potentially due to partial dissolution of non-cross-linked CMC in blood or plasma, the paste gradually lost its mechanical strength. It is observed that the interface of paste with the tissue dissociated, potentially resulting in re-bleeding. Thus, the non-crosslinked CMC hemostatic paste has failed in longer term hemostatic evaluation.

Figure 17:
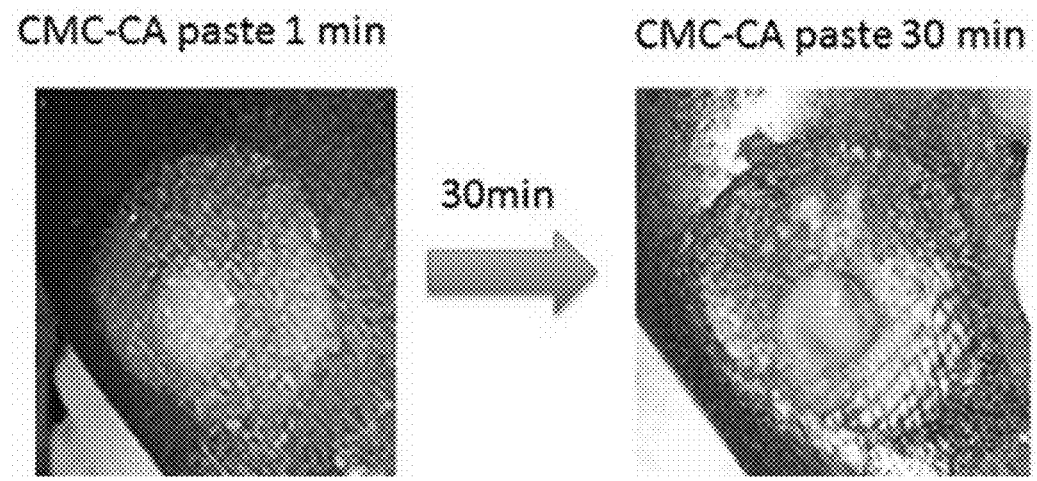
FIG. 17 shows the testing results of the hemostatic paste containing CMC-CA (inventive example).

Referring to FIG. 17, the testing results of the hemostatic paste formulated as described in Example 1, using CMC-CA, is presented (inventive example). The inventive hemostatic paste achieved hemostasis in under 1 minute, as shown, in heparinized liver punch model. After 30 minutes, no re-bleeding was observed. Thus, the instant crosslinked CMC-CA based paste exhibited superior hemostatic properties due to its 3D polymer net structure with better mechanical and dissolution strength compared with pure non-cross-linked CMC.

Example 9. Hemostatic Paste Properties in Animal Model: Hemostasis Data for Cross-Linked Starch Vs. Cross-Linked CMC Based Paste The hemostatic paste formulated as described in Example 1 was further evaluated in liver punch model (porcine), comparing the inventive paste formulated with citric acid cross-linked CMC (CMC-CA) and paste with CMC-CA xerogel replaced with the cross-linked starch.

Figure 18:
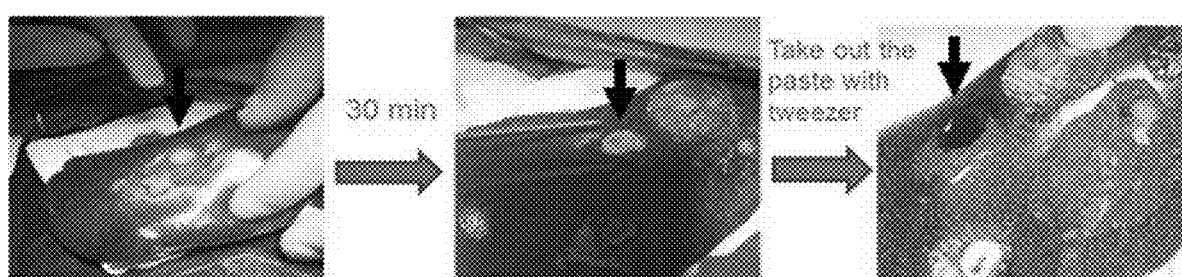
FIG. 18 shows the testing results of the hemostatic paste containing CA cross-linked carboxymethyl starch (comparative example).

Referring to FIG. 18, the testing results of the hemostatic paste formulated as described in Example 1, but using CA cross-linked carboxymethyl starch, is presented (comparative example). Citric acid cross-linked carboxymethyl starch paste was applied onto the liver punch model. While it has achieved hemostasis at 1 min, continuing observation for 30 minutes indicated that the comparative paste became dry and began to dissociate with the liver tissue. Further it was shown that it was relatively easy to remove the paste compact from the punch hole with a tweezer. To the contrary, the inventive CMC-CA based paste does not exhibit this dissociation from tissue phenomenon even after 30 min, as shown in FIG. 17. Based on this evaluation, the inventive crosslinked CMC-CA based paste exhibited superior hemostatic properties when compared to cross-linked starch based paste which showed poor tissue adhesion.

Example 10. Hemostatic Paste Adhesion to the Tissue: Comparative Testing

Figure 19:
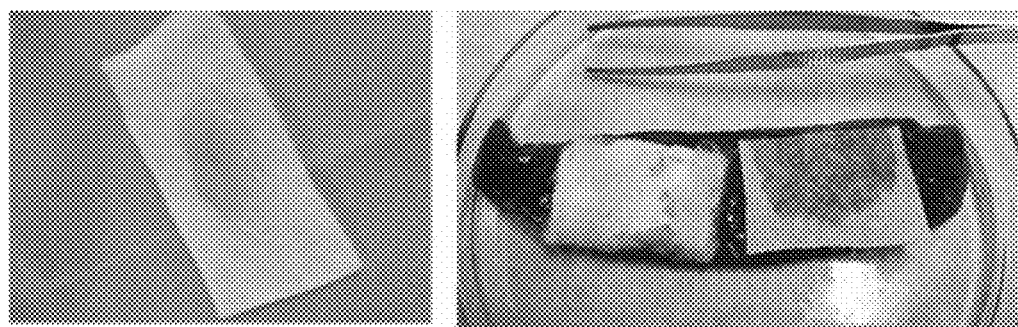
FIG. 19 shows the testing of the adhesion to the tissue.

Referring now to FIG. 19, testing the adhesion to the tissue was further evaluated as follows. The inventive CMC-CA based hemostatic paste and comparative hemostatic pastes were applied onto backing materials, including commercially available Oxidized Regenerated Cellulose (ORC)-based non-woven pad and synthetic polymer polyglactin 910 (copolymer made from 90% glycolide and 10% L-lactide, PG910)-based non-woven pad, as shown. Then the patches were applied to the porcine liver tissue. After a 1 min tamponade by hand, the patches were peeled off from the liver tissue by forceps. The peeling force, which represented the adhesive force of each hydrogel, was evaluated and was ranked from 1 to 5. Referring to Table 6, adhesiveness evaluations are presented, with 5 being most adhesive; 1 being not adhesive, for the inventive CMC-CA based paste, and for comparative pastes based on pregelatinized starch hydrogel and on CMC-CA/pregelatinized starch 1:1 mixture.

TABLE 6

Tissue adhesiveness evaluation (5-most adhesive; 1-not adhesive)

| Sample | Adhesiveness |
|---|---|
| CMC-CA hydrogel based paste (inventive) | 5 |
| Pregelatinized starch hydrogel (comparative) | 2 |
| CMC-CA/pregelatinized starch 1:1 (comparative) | 3 |

Based on this evaluation, the inventive crosslinked CMC-CA based paste exhibited superior hemostatic properties of tissue adhesion when compared to Pregelatinized starch hydrogel based paste and CMC-CA/pregelatinized starch 1:1 based pastes.

Example 11. Hemostatic Paste Properties in Animal Model

Figure 20:
FIG. 20 shows the inventive CMC-CA based hemostatic paste prior, during application, and after application into liver punch model.
Figure 20:
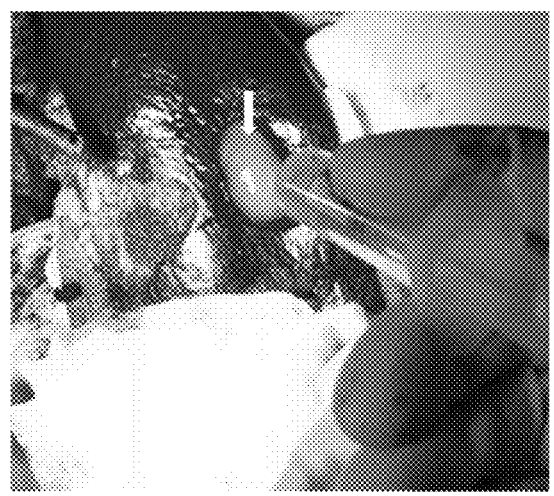
Figure 20:
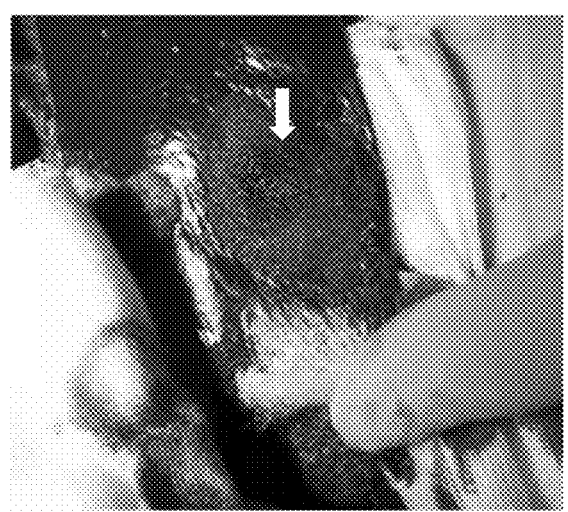

The hemostatic paste formulated as described in Example 1 was further evaluated in liver punch model (porcine). Referring to FIG. 20, inventive CMC-CA based hemostatic paste is shown prior, during application, and after application into liver punch model, as pressed into narrow wound, with the hemostasis achieved within 1 min.

Example 12. Hemostatic Paste on a Substrate—Properties in Animal Model

Figure 21:
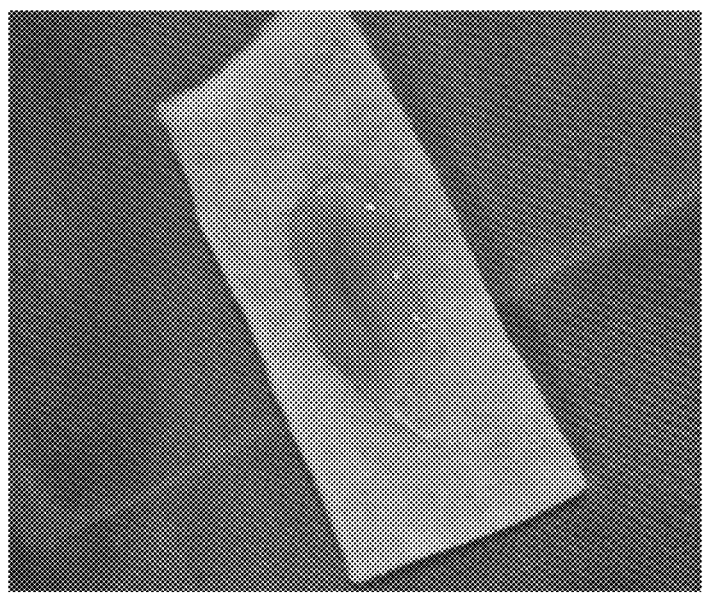
FIG. 21 shows the inventive CMC-CA based hemostatic paste applied to commercially available Oxidized Regenerated Cellulose (ORC)-based non-woven pad.
Figure 22:
FIG. 22 shows the CMC-CA based hemostatic paste applied to commercially available Oxidized Regenerated Cellulose (ORC)-based non-woven pad and the resulting composite prior to being tested for adhesion to a liver tissue coupon, and after contacting with liver tissue coupon.
Figure 22:

The inventive CMC-CA based hemostatic paste was applied onto backing materials comprising a pad or a gauze for applications onto broader areas of tissue to address surface bleeding or oozing. Referring now to FIG. 21 inventive CMC-CA based hemostatic paste is shown applied to commercially available Oxidized Regenerated Cellulose (ORC)-based non-woven pad. Referring now to FIG. 22, the resulting composite is shown prior to being tested for adhesion to a liver tissue coupon, and after contacting with liver tissue coupon.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A flowable hemostatic paste comprising:
   A xerogel crosslinked milled polysaccharide dispersed within a substantially anhydrous blend of:
   i. A glycerol-containing dispersant, and
   ii. An alcohol-functionalized dispersant selected from the group consisting of propylene glycol and 1,3-Butanediol or mixtures thereof,
   wherein the paste has a moderate viscosity at rest and room temperature and provides a substantially homogenous dispersion of the crosslinked polysaccharide, and wherein:
   (i) said paste comprises a weight ratio of propylene glycol to glycerol of from about 1:0.5 to about 1:2;
   (ii) said paste further comprises an alkaline agent; and/or
   (iii) the weight ratio of cross-linked polysaccharide to glycerol-containing dispersant ranges from about 0.9 to about 1.25.

2. The hemostatic paste of claim 1, wherein said alkaline agent comprises sodium hydroxide, present at about 0.1-3%.

3. The hemostatic paste of claim 1, wherein the cross-linked polysaccharide comprises a carboxymethyl cellulose (CMC) that is cross-linked by reaction via a polyfunctional carboxylic acid, wherein said acid is selected from the group consisting of malic, tartaric, citric, malonic, succinic, glutaric, or adipic acid or mixtures thereof.

4. The hemostatic paste of claim 3, wherein said acid is citric acid.

5. The hemostatic paste of claim 4, wherein said paste comprises:
   35% to 65% by weight of citric acid cross-linked CMC, which is suspended or dispersed in powder form in a viscous liquid mixture of a glycerol-containing hygroscopic dispersant and an alcohol-functionalized dispersant of: propylene glycol, 1,3-Butanediol or mixtures thereof.

6. The hemostatic paste of claim 5, wherein said cross-linked CMC is a suspended powder having average particle size less than 100 microns.

7. The hemostatic paste of claim 6, wherein said paste comprises less than 1% of water.

8. The hemostatic paste of claim 6, wherein said paste comprises
   a. about 49-55% of citric acid cross-linked CMC;
   b. about 18-30% of glycerol;
   c. about 15-30% of propylene glycol.

9. The hemostatic paste of claim 6, wherein said paste is supported on a substrate that is a flexible bioabsorbable sheet.

10. The hemostatic paste of claim 9, wherein said substrate comprises oxidized cellulose or polyglactin 910.

11. The hemostatic paste of claim 6, wherein said paste is disposed in a squeezable tube.

12. A method of making a wound dressing containing the hemostatic paste of claim 6, comprising the steps of applying said hemostatic paste onto at least one face of a flexible bioabsorbable sheet substrate.

13. A method of making a wound dressing according to claim 12, wherein the flexible bioabsorbable sheet is in the form of a woven mesh, structured felt, unstructured felt, film, powder or combinations thereof, and contains one or more layers of oxidized cellulose, hemostatic polymeric blends, or mixtures thereof.

14. A method of using the hemostatic paste of claim 6, comprising the steps of applying said hemostatic paste, optionally supported on a flexible absorbable sheet substrate, to a bleeding tissue or wound.

* * * * *